United States Patent [19]

Grouiller

[11] Patent Number: 4,912,174

[45] Date of Patent: Mar. 27, 1990

[54] PROCESS OF PREPARATION OF A NEW MEMORY THERMOPLASTIC COMPOSITION FROM POLYCAPROLACTONE AND POLYURETHANE, PRODUCT OBTAINED BY THIS PROCESS AND ITS USE PARTICULARLY IN ORTHOPEDICS

[75] Inventor: Hervé Grouiller, Arcenant, France

[73] Assignee: Laboratoires D'Hygiene et de Dietetique (L.H.D.), Paris, France

[21] Appl. No.: 803,605

[22] Filed: Dec. 2, 1985

Related U.S. Application Data

[63] Continuation of Ser. No. 537,408, filed as PCT FR83/00016 on Jan. 20, 1983, abandoned.

[30] Foreign Application Priority Data

Jan. 20, 1982 [FR] France ............................ 82 00854

[51] Int. Cl.$^4$ .............................................. C08L 75/04
[52] U.S. Cl. .................................... 525/415; 525/455; 525/903
[58] Field of Search ......................... 525/415, 455, 903

[56] References Cited

U.S. PATENT DOCUMENTS 4,098,743 7/1978 Scriven et ál. ...................... 525/415

*Primary Examiner*—Ana L. Carrillo
*Attorney, Agent, or Firm*—Foley & Lardner, Schwartz, Jeffery, Schwaab, Mack, Blumenthal & Evans

[57] ABSTRACT

A process is disclosed for preparing a thermoplastic composition having elastic memory and containing polyurethane interlocked in a network of polycaprolactone. The product of the aforementioned process is particularly useful as orthopedic cast or immobilizing device.

19 Claims, No Drawings

//4,912,174

PROCESS OF PREPARATION OF A NEW MEMORY THERMOPLASTIC COMPOSITION FROM POLYCAPROLACTONE AND POLYURETHANE, PRODUCT OBTAINED BY THIS PROCESS AND ITS USE PARTICULARLY IN ORTHOPEDICS

This is a continuation, of application Ser. No. 537,408, filed as PCT FR83/00016 on Jan. 2, 1983, now abandoned.

BACKGROUND OF THE INVENTION

The present invention relates to a process of preparation of a new memory thermoplastic composition from polycaprolactone and polyurethane. It relates also as new industrial product, to the thermoplastic composition obtained by this process. It relates also to the use of this new industrial product particularly in orthopedics as immobilising means.

It is known that the material most used to immobilise a part of the human body, and particularly a broken limb, is plaster. It is found that, in the field of orthopedic structure, bandages with plaster constitute immobilising means having a large number of drawbacks. In fact, plaster is heavy and little permeable to air, it absorbs and disperses X-rays, which hinders diagnosis by radiography, and it often gives rise to irritation of the skin.

It is also known that, to replace the plaster, it has been proposed in the past to use orthopedic structures of polycaprolactone. Polycaprolactone is a substance which has at room temperature high bending strength and high modulus elasticity, but which has the drawback from 50° C. of becoming soft and very sticky. If polycaprolactone sheet is heated to a temperature above about 50° C., it rapidly loses its mechanical strength and its elasticity, and it cannot even support its own weight.

SUMMARY OF THE INVENTION

It has been found surprisingly that, from polycaprolactone (abbreviated PCL) and polyurethane (abbreviated PU), there is obtained by the operational methods defined below, a new thermoplastic composition constituting an industrial product which is endowed with elastic memory and which has particularly interesting properties as regards mechanical strength when hot. This product, which is particularly useful as orthopedic setting means, (i) is, with respect to plaster, easier to use and lighter in weight, and (ii) does not lose entirely, with respect to the PCL, its mechanical strength, particularly at 60° C.

DETAILED DESCRIPTION OF THE PREFERRED EMBODIMENTS

The process of preparation of a memory thermoplastic composition from polycaprolactone and from polyurethane, according to the invention, is characterised in that the formation of the polyurethane from at least one polyol and from at least one polyisocyanate is carried out within the polycaprolactone.

The simple mixing of PCL with previously polymerised PU not being suitable from the point of view of the mechanical properties, it is very important, according to the invention, for the formation of the polyurethane from polyol and from polyisocyanate to be effected or to be continued in the polycaprolactone in the softened state, so that the polymerisation of the PU is effected with interlocking of the network of the weakly thermoplastic or non-thermoplastic PU, in the highly thermoplastic network of the PCL. In brief, it will be possible for this purpose to employ two variations A and B, variation A being the preferred variation:

Variation A

Mix the PCL with the means forming the PU, namely the polyols and the polyisocyanates, and then proceed with the polymerisation reaction of the PU;

Variation B

Initiate the polymerisation reaction forming the PU from its constituent compounds, mix the resulting reaction medium with the PCL so that the polymerisation of the PU continues in the PCL.

According to an advantageous embodiment of of the present invention, the formation of the PU is carried out by the operational methods given above, from a means I selected from among the group constituted by polyisocyanates and their mixtures, and a means II selected from the group constituted by polyols and their mixtures, the means I and II being such that before the polymerisation reaction, the number of free NCO groups of means I is substantially equal to the number of free OH groups of means II.

Advantageously, the thermoplastic product according to the invention will be prepared by the reaction of means I and II in the PCL, so that a final composition is obtained comprising:

(A) - 60 to 100 parts by weight of PCL, and (B) - 2 to 40 parts by weight of PU.

If necessary, the formation of the PU in the PCL will be carried out in the presence of one or several adjuvants, particularly at least one means selected from among the group constituted by inorganic fillers, colouring matters and plasticisers. It will thus be possible to use per 60 to 100 parts by weight of PCL (C) - at the most 35 parts by weight of inorganic filler, and/or (D) - at the most 5 parts by weight of plasticising agent.

The preferred amounts are from 5 to 35 parts by weight for the means C and from 1 to 2 parts by weight for the means D, when, of course, means C and/or D are used. Among mineral fillers which are suitable, may be mentioned particularly ZnO, CaCO$_3$, TiO$_2$, Ta$_2$O$_5$ and talc; and among plasticisers which are suitable, may be mentioned particularly stearic acid which plays also the role of lubricating agent.

The best method of practising the process of the invention comprises 1. the mixture with stirring of the PCL with the means I and II, at a temperature comprised between 75 and 130° C., for 1 to 10 minutes, to initiate the formation of the PU in the PCL network, then 2. the continuation of the formation of the PU in the network of the PCL at a temperature higher than or equal to 60° C. (and preferably comprised between 60° C. and 100° C.), for 10 to 30 minutes.

The means C and/or C, when they are present, will be incorporated at stage 1.

Advantageously, it is recommended at stage 1. to carry out malaxation in a fluid type kneader, at 50–300 r.p.m., and preferably at 150 r.p.m. The malaxation can be carried out under a nitrogen atmosphere particularly when it is effected at a temperature comprised between 100 and 130° C. Preferably, it is recommended to carry out the malaxation at 80° C., for 5 minutes, at 150 r.p.m.

As indicated above, it is recommended that at the stage 1, the means I and II should be such that the number of free NCO groups of the means I is substantially equal to the number of free OH groups of the means II.

At stage 2 it is recommended advantageously to pursue the polymerisation of the PU in the PCL at a temperature of the order of about 60° C. to about 80° C., for about 20 minutes.

In certain cases, it will be observable that the polymerisation of the PU in the network of the PCL is not completed at the end of stage 2; said polymerisation will then be left to continue by itself during cooling which takes place generally after stage 2, or during storage after stripping.

In addition, accordingly to the final destination of the product, the stage 2 may be employed in the course of a moulding operation [moulding at a temperature of 60 to 100° C. (preferably at a temperature of 60 to 80° C.) for 10 to 30 minutes (preferably for 20 minutes) in the case of use in orthopedics], may be followed by moulding (also in the case of use in orthopedics), or again may be followed by an extrusion operation (particularly in the case of other uses).

The means I which are suitable are polyisocyanates containing at least 2 free NCO groups per molecule. Among those may be mentioned particularly (i) the di-, tri- and tetra-isocyanates of formula $R(NCO)_n$, (where n is a whole number having a value comprised between 2 and 4, and R is particularly an aliphatic, cycloaliphatic, aryl or aralkyl group comprising from 4 to 15 carbon atoms) such as 2,4-toluenediiasocyanate, 2,6-toluenediisocyanate, 4,4'-diphenylmethanediisocyanate, 1,6-hexamethylenediisocyanate, 1,4-cyclohexanediisocyanate, 4,4'-dicyclohexylmethanediisocyanate, and isophoronediisocyanate (i.e. the diisocyanate derived from 2,6-dimethyl-2,5-heptadiene-4-one), (ii) prepolymers of the polyurethane type containing free NCO groups and obtained by the reaction of an excess polyisocyanate with a polyol, a polyolether and/or a polyolester, and (iii) their mixtures.

Among the means I mentioned above, the most preferred polyisocyanates are 2,4-toluenediisocyanate, 2,6-toluenediisocyanate and 4,4'-diphenylmethanediisocyanate, the preferred means being 2,4-toluenediisocyanate and commercial toluenediisocyanate which contains 80% by weight of 2,4 isomer and 20% by weight of 2,6 isomer.

The means II which are suitable are polyols containing at least 2 free OH groups per molecule. Among the latter may be mentioned particularly polyetherpolyols having an equivalent molecular weight comprised between about 80 and about 400, and containing at least 2 free OH groups per molecule. These polyether-polyols are generally obtained by condensation of an alkylene oxide (abbreviated OA) such as ethylene oxide and propylene oxide with a diol such as ethyleneglycol, propyleneglycol, diethyleneglycol, hexamethyleneglycol, tetramethyleneglycol and cyclohexyl-1,4-dimethanol, a triol, a tetraol such as pentaerythritol, a pentol, a hexol such as dulcitol and sorbitol, and their mixtures. This condensation is carried out generally in the proportion of 1 to 20 OA groups per free OH group of polyol.

Among polyols II which are suitable may be mentioned particularly polyester-polyols such as the products marketed under the name "ISONOL" RMJ 101 and RMJ 104 by the UPJOHN company, and under the name "SCURANOL" P 440, P 460, P 4004 and P 4001 by the RHONE-POULENC company.

Advantageously it is possible to use commercially available polyether-polyols and in particular products manufactured and marketed by the PECHINEY-UGINE-KUHLMANN company under the names UGIPOL 1004, 1010, 1020, 1061, 1092 and 1093 which are condensation products of alkylene oxide with one or several diols, UGIPOL 1130, 1131, 1171, 1180, 1340 1370, 1371 and 1372 which are condensation products of alkylene oxide with one or several triols, UGIPOL 3310, 3320, 3400, 3420, 3450, 3460 and 3602 which are condensation products of alkylene oxide with one or several tetraols, pentols and/or hexols.

The product obtained at stage 2, which contains (A) 60 to 100 parts by weight of PCL (B) 2 to 40 parts by weight of PU, and if necessary, the means C and/or D, is useful in several applications. It is particularly suitable as orthopedic setting means, in accordance with the present invention; it is also suitable as (i) means for detecting heat, (ii) insulating or connecting means, particularly in the field of seals and that of protective sheaths for electrical conductors and (III) means for fastening inserts particularly for replacing pegs, as indicated respectively in French patent applications n°82-00857 and n°82-00858, filed the same day as the present invention.

There will now be considered the application of the product according to the invention as orthopedic setting means. The product is obtained according to three modifications $A_1$ and $B_1$ (discontinuous) and $C_1$ (continuous):

Modification $A_1$: after stage 1 the malaxation is stopped, stage 2 placed in operation in the kneader, then the resulting product is molded or rolled;

Modification $B_1$: after stage 1 stage 2 is placed in operation in a mold; and

Modification $C_1$: stage 1 is carried out continuously in a fluid-tight kneader, then continuously the resulting mixture is injected into molds where stage 2 is put in operation.

A product is obtained (particularly in the form of a disc or sheet) having a thickness comprised between about 1mm and about 7mm, and preferably between 2.5mm and 4.5mm.

For use as orthopedic setting means, it is recommended advantageously to employ stage 1 so that there is a final composition containing (A) - 60 to 95 parts by weight of PCL, and (B) - 5 to 40 parts by weight of PU, in association, if necessary, with means C and/or D. Thus a final thermoplastic product is provided which may be easily shaped and re-shaped hot (hence reuseable), which is endowed with an elastic memory, which is rigid at room temperature and/or the temperature of the body, which softens from 55° C. whilst keeping a part of its mechanical strength at 60° C., and which possesses the advantage of not being opaque to X-rays.

Other advantages and characteristics of the invention will be better understood on reading the following examples of preparation which are in no way limiting but given by way of illustration.

EXAMPLE 1

(a) In a fluid-tight bladed kneader in which a temperature of 80° C. and a stirring of 150 rpm is maintained, are introduced successively 800 g of polycaprolactone (producted marketed by the by the UNION CARBIDE company under the name "PCL 700" and having an average molecular weight of about 40,000);

when the polycaprolactone is softened (that is to say about 2 to 5 minutes after the introduction of the PCL), 70 g of polyether-polyol (product marketed by the PECHINEY-UGINE-KUHLMANN company under the name of "UGIPOL 3602" and having an equivalent molecular weight of about 140), then when the resulting mixture is softened and homogeneous (that is to say about 2 to 5 minutes after the introduction of the polyether-polyol), the stoichiometric amount (43 g) of 2,4-toluenediisocyanate.

The resulting mixture is kept at 80° C. with stirring (150 rpm) for 10 minutes.

(b) The stirring is stopped and the mixture so obtained left to stand in the kneader at 80° C. for 10 minutes.

(c) The mixture so obtained is poured into a rectangular mold and pressed at 80° C. for 10 minutes. A sheet having a thickness comprised between 2 and 4 mm is obtained which is left to cool to ambient temperature (15°–20° C.).

EXAMPLE 2

(a) Procedure was as indicated in Example 1 (a) with a fluid-tight screw kneader replacing the 2,4-toluenediisocyanate by commercial toluenediisocyanate which comprises 80% by weight of 2,4 isomer and 20% by weight of 2,6 isomer.

(b) The mixture so obtained was continuously injected into molds and pressed at 80° C. for 20 minutes.

(c) The molds were cooled to room temperature and from each mold was obtained a sheet having a thickness of 3 to 3.5 mm.

EXAMPLE 3

(a) Procedure was as indicated in Example 1 (a) from 700 g of PCL ("PCL 700"), from 25 g of polyether-polyol ("UGIPOL 3602") and from 15 g of commercial toluenediisocyanate.

(b) The mixture so obtained was poured into a mold and pressed at 75° C. for 20 minutes.

(c) The mold was cooled to room temperature to obtain a sheet having a thickness of 3 mm.

EXAMPLE 4

(a) Into a fluid-tight bladed kneader, in which a temperature of 75° C. and stirring of 200 rpm are maintained, are introduced successively:

1000 g of polycaprolactone (having an average molecular weight of about 35,000);

when the PCL is softened, 100 g of polyether-polyol (50 g of "UGIPOL 3602" and 40g of "UGIPOL A004"), then when the resulting mixture is softened and homogeneous 50g of commercial teluenediisocyanate.

The temperature is kept at 75° C. and stirring at 200 rpm for 8 minutes.

(b) The stirring is stopped and the polymerisation reaction of the PU is left to develop for 10 minutes at 80° C.

(c) The resulting mixture is poured into a mold and pressed at 60° C. for 10 minutes. A sheet of 4 mm thickness is obtained.

EXAMPLE 5

By proceeding as indicated in Example 2 from the required amounts of PCL, UGIPOL 3602 and 4,4'-diphenylmethanediisocyanate, a sheet of 3 to 4mm thickness is obtained containing 80 parts by weight of PCL and 20 parts by weight of PU.

EXAMPLE 6

Into a bladed kneader in which is maintained, under a nitrogen atmosphere, a stirring of 180 r.p.m., is prepared a prepolymerisate of means I and II by reaction at 110°–130° C., for 2 to 5 minutes, of 100 parts by weight of "TERACOL 1000" [mixture of polytetramethyleneetherglycols of the formula

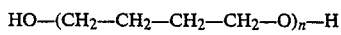

where n is a number comprised between 6 and 42 and has an average value 13.63, manufactured by the DUPONT DE NEMOURS Company] previously heated to 100°–105° C. for less than 1 hour under vacuum to remove traces of moisture, with 53 parts by weight of 4,4'-diphenyl-methanediisocyanate previously heated to 70° C.

In the reaction mixture thus obtained is introduced at 75° C. with stirring and under a nitrogen atmosphere 13.4 parts by weight of stearic acid, then 502.5 parts by weight of PCL having a molecular weight of about 40,000, and finally 14.4 parts by weight of 1,4-cyclohexyl-dimethanol. The mixture thus obtained is left under stirring for 5 minutes at 75° C. to continue the polymerisation of the PU.

The resulting mixture is then run into rectangular moulds and pressed at 100° C. for 20 minutes to obtain, after cooling at 15°–20° C., sheets having a thickness of 3 to 3.5 mm.

Under these operational conditions where the 1,4-cyclohexyl-dimethanol, TERACOL 1000 and 4,4'-diphenylmethanediisocyanate are in a molar ratio of about (1:1:2), a final sheet product is obtained containing approximately 2 parts by weight of stearic acid, and 25 parts by weight of PU interlocked in the network of 75 parts by weight of PCL.

EXAMPLE 7

By proceeding as indicated in Example 6 from 100 parts by weight of "TERACOL 1000", 53 parts by weight of 4,4'-diphenylmethanediisocyanate, 19.4 parts by weight of stearic acid, 805 parts by weight of PCL of molecular weight about 40,000, and 11.8 parts by weight of 1,6-hexanediol, are obtained, after molding, sheets of 3 to 3.5 mm thickness, the final sheet product containing approximately 2 parts by weight of stearic acid, and 17 parts by weight of PU interlocked in the network of 83 parts by weight of PCL.

The sheets according to the invention, and in particular those of examples 1 to 5, lend themselves easily to molding on the portion of the surface of the body which needs orthopedic immobilising means, without force being necessary to stretch them. They are heated to 60° C., particularly by immersion in water at this temperature before applying them to the skin. When hot, they are self-adhesive and adhere well to one another on simple pressure. After cooling, they have very good resistance to separation, high rigidity, cutting up then being done with scissors. After manipulation it is observed that they do not show any trace of the fingers of the manipulator, and after application to a portion of the skin and then cutting up to be removed there is observed on the inner surface of the splint the impressions of the skin (pores, lines of the hand, etc.); these findings and observations show that the sheets according to the invention, due to the fact of their elasticity, avoid by slight retraction any wobbling of the splint without occasioning excessive pressure on the surface to be molded.

In other applications described in the above-indicated French patent applications, advantageously products obtained at stage 2 according to the invention will be used containing:

(i) for use as heat detection means:
(A) 80 to 95 parts by weight of PCL, and
(B) 5 to 20 parts of PU;
(ii) for use particularly as insulating or connecting means (protective seals and sheets):
(A) 100 parts by weight of PCL, and
(B) 5 to 50 parts by weight of PU;
(iii) for use as fastening means (inserts)
(A) 60 to 100 parts by weight of PCL, and
(B) 5 to 40 parts by weight of PU.

I claim:

1. A process for preparing a water-insoluble thermoplastic composition having elastic memory and containing polycaprolactone and polyurethane, comprising the steps of (a) forming a mixture comprising at least one polyol, at least one polyisocyanate and from 60 to 100 parts by weight unmodified polycaprolactone, the amounts of polyol and isocyanate in said mixture being such that the number of free NCO groups of the isocyanate is substantially equal to the number of free OH groups of said polyol and the total amount of polyol and polyisocyanate producing from 2 to 40 parts by weight polyurethane when reacted with each other; and (b) polymerizing said polyol and said polyisocyanate with each other in the presence of said unmodified polycaprolactone to form said polyurethane interlocked in the network of said polycaprolactone.

2. A process according to claim 1, wherein said polyisocyanate is selected from the group consisting of 2,4-toluenediisocyanate, 2,6-hexamethylenediisocyanate, 1,4-cyclohexanediisocyanate, 4,4'-dicyclohexylmethanediisocyanate, isophoronediisocyanate and mixtures thereof.

3. A process according to claim 1, wherein said polyol is selected from the group of polyetherpolyols obtained by condensation of (A) an alkylene oxide selected from the group consisting of ethylene oxide and propylene oxide with (B) (i) a diol selected from the group consisting of ethyleneglycol, propyleneglycol, diethyleneglycol, hexamethyleneglycol, tetramethyleneglycol and cyclohexyl-1,4-dimethanol, (ii) pentaerythritol, or (iii) a hexol selected from the group consisting of dulcitol and sorbitol, the condensation being carried out in the proportion of about 1 to about 20 epoxide groups per free OH groups.

4. A process according to claim 1, wherein said polyol is a polyether-polyol corresponding to the formula $$HO-(CH_2-CH_2-CH_2-CH_2-O)_n-H$$

where n is a number between 6 and 42.

5. A process according to claim 1, wherein the formation of the polyurethane is carried out in the presence of at least one substance selected from the group consisting of inorganic fillers, coloring agents and plasticizers.

6. A process according to claim 5, wherein said inorganic filler comprises at the most 35 parts by weight per 60 to 100 parts of polycaprolactone.

7. A process according to claim 5, wherein said plasticizer comprises at the most 5 parts by weight per 60 to 100 parts by weight of polycaprolactone.

8. A process according to claim 1, which comprises the steps of:
mixing while stirring polycaprolactone with said polyisocyanate and said polyol at a temperature between 75° C. and 130° C. for 1 to 10 minutes to initiate formation of the polyurethane in the network of the polycaprolactone, then
continuing the polymerization of the polyurethane in the network of the polycaprolactone at a temperature of at least 60° C. for 10 to 30 minutes.

9. A process according to claim 1, which comprises the steps of:
mixing with stirring of the polycaprolactone with a reaction mixture resulting from prepolymerization of said polyisocyanate and said polyol at a temperature between 75° C. and 130° C. for 1 to 10 minutes to initiate the formation of the polyurethane in the network of the polycaprolactone, then
continuing the polymerization of the polyurethane in the network of the polycaprolactone at a temperature of at least 60° C. for 10 to 30 minutes.

10. A process according to claim 8, further comprising the step of molding the resulting composition after said polymerization.

11. A process according to claim 8, further comprising the step of molding the resulting composition during said polymerization.

12. A process according to claim 9, further comprising the step of molding the resulting composition after said polymerization.

13. A process according to claim 9, further comprising the step of molding the resulting composition during said polymerization.

14. An orthopedic immobilizing device produced by the process of claim 10.

15. An orthopedic immobilizing device produced by the process of claim 11.

16. A process according to claim 1, wherein said polyol and said polyisocyanate are mixed together and thereafter mixed with said unmodified polycaprolactone.

17. A water-insoluble thermoplastic composition having elastic memory and containing polycaprolactone and polyurethane, said composition being the product of a process comprising the steps of (a) forming a mixture comprising at least one polyol, at least one polyisocyanate and from 60 to 100 parts by weight unmodified polycaprolactone, the amounts of polyol and isocyanate in said mixture being such that the number of free NCO groups of the isocyanate is substantially equal to the number of free OH groups of said polyol and the total amount of polyol and polyisocyanate producing from 20 to 40 parts by weight polyurethane when reacted with each other; and (b) polymerizing said polyol and said polyisocyanate with each other in the presence of said unmodified polycaprolactone to form said polyurethane interlocked in the network of said polycaprolactone.

18. A thermoplastic composition according to claim 17, wherein said polyol and said polyisocyanate are mixed together and thereafter added to said unmodified polycaprolactone.

19. A thermoplastic composition according to claim 17, which comprises
(A) 60 to 95 parts by weight of unmodified polycaprolactone, and
(B) 5 to 40 parts by weight of polyurethane.

* * * * *